United States Patent

Hagiwara et al.

Patent Number: 5,827,524
Date of Patent: Oct. 27, 1998

[54] ANTIMICROBIAL POLYMER COMPOSITION

[75] Inventors: Zenji Hagiwara, Kusatsu; Kazuo Kishimoto; Hiroshi Yamazaki, both of Tokyo, all of Japan

[73] Assignees: Hagiwara Research Corporation, Osaka; Japan Electronic Materials Corporation, Hyogo-Ken, both of Japan

[21] Appl. No.: 584,001

[22] Filed: Jan. 11, 1996

[30] Foreign Application Priority Data

Jan. 12, 1995 [JP] Japan ................................ 7-018794

[51] Int. Cl.⁶ .................................................. A61K 9/10
[52] U.S. Cl. ........................ 424/409; 424/486; 424/487; 424/488; 424/499; 424/501; 523/122
[58] Field of Search ............................ 424/405, 409, 424/411, 9.411, 9.4, 486–488, 499, 501; 428/402; 523/210, 211, 122; 502/243, 407

[56] References Cited

FOREIGN PATENT DOCUMENTS 0251783  1/1988  European Pat. Off. .
0116865  8/1994  European Pat. Off. .

*Primary Examiner*—Edward J. Webman
*Attorney, Agent, or Firm*—Roylance, Abrams, Berdo & Goodman, L.L.P.

[57] ABSTRACT

The present invention relates to a novel antimicrobial polymer composition comprising a novel crystalline antimicrobial composition. More particularly, the present invention relates to an antimicrobial polymer composition comprising a crystalline antimicrobial composition and a polymer, wherein said crystalline antimicrobial composition comprises a crystalline silicon dioxide containing silver ions and one or two optional metal ions selected from the group consisting of zinc and copper.

7 Claims, 1 Drawing Sheet

ANTIMICROBIAL POLYMER COMPOSITION

BACKGROUND OF THE INVENTION

The present invention relates to a novel antimicrobial polymer composition comprising a novel crystalline antimicrobial composition.

An antimicrobial composition having an antimicrobial aluminosilicate provided coating on the surface of silica gel, wherein said aluminosilicate containing metal ions having a microbicidal action selected from the group consisting of silver, zinc, copper, mercury, tin, lead, bismuth, cadmium, and chromium is known. Since said antimicrobial composition is effective against common fungi and also exhibits excellent biocidal activity against mildew, research and development leading to new applications has been carried out. An antimicrobial polymer composition comprising said antimicrobial composition is disclosed in Japanese Patent Publication (kokoku) No. 39368/94 and U.S. Pat. No. 5,244,667.

However, if said inorganic silica gel based amorphous antimicrobial composition is added to a polymer and molded under heating, it is known that an undesirable discoloration or coloring occurs and also properties of the molded article vary over time. Since these problems have remained unresolved. In some applications of the antimicrobial composition, the above phenomena are serious and should be resolved.

The object of the present invention is to dissolve the above problems. The present inventor has found that a crystalline antimicrobial composition obtained from amorphous antimicrobial composition, of which main component is silica gel, is capable of improving a physical property, heat resistance and weatherability, as well as improving a weatherability of the antimicrobial polymer composition.

Furthermore, an antimicrobial polymer composition comprising the novel crystalline antimicrobial composition exhibits excellent biocidal activity and weatherability, also heat resistance and discoloration resistance thereof are far superior to those of a composition comprising a known inorganic antimicrobial compound.

SUMMARY OF THE INVENTION

The present invention provides an antimicrobial polymer composition comprising a crystalline antimicrobial composition and a polymer, wherein said crystalline antimicrobial composition comprises a crystalline silicon dioxide containing silver ions and one or two optional metal ions selected from the group consisting of zinc and copper.

The present invention also provides a process for preparing an antimicrobial composition of said antimicrobial polymer composition comprising steps of 1) preheating an antimicrobial composition having an antimicrobial coating of an aluminosilicate provided on the surface of silica gel, wherein said aluminosilicate contains silver ions and one or two optional metal ions selected from the group consisting of zinc and copper, to a temperature between 250° and 500° C. to substantially remove water, 2) sintering at a temperature from 800° to 1300° C., and 3) mixing the obtained crystalline antimicrobial composition with a polymer.

DETAILED DESCRIPTION OF THE INVENTION

Figure 1:
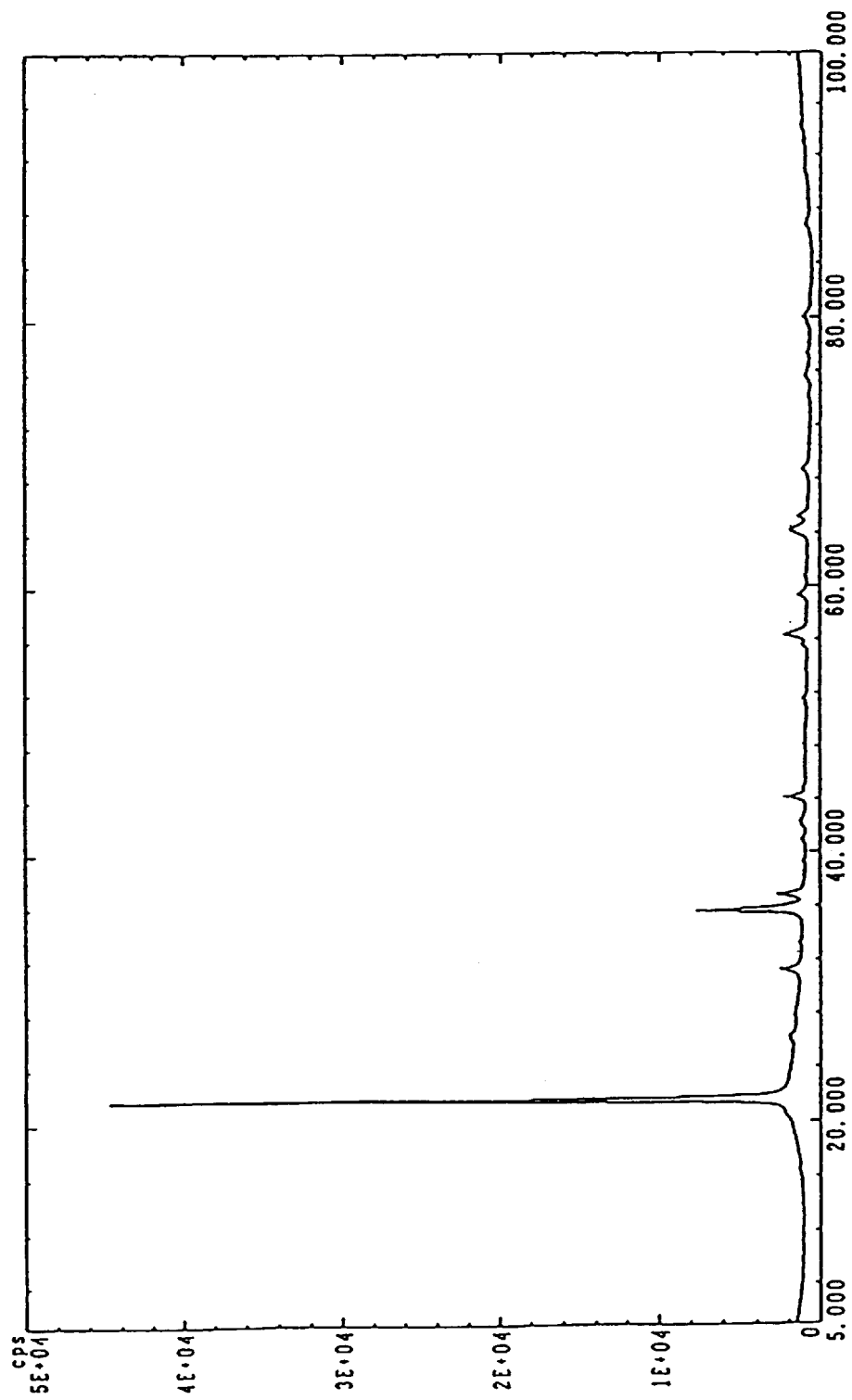
FIG. 1 shows an X-ray diffraction spectrum of the antimicrobial composition of sample 7 (Ag=3.7%, Zn=2.0%: Dav=3.77 microns). The ordinates axis represents relative intensity and the transverse axis represents a diffraction angle.

The present invention provides an antimicrobial polymer composition comprising a crystalline antimicrobial composition and a polymer, wherein said crystalline antimicrobial composition comprises a crystalline silicon dioxide containing silver ions and one or two optional metal ions selected from the group consisting of zinc and copper.

A crystal form of the crystalline silicon dioxide is not restricted. However, a cubic or cristobalite system are preferred. A crystalline ratio is not restricted either. However, the antimicrobial composition obtained by the thermal treatment is desirable to have a crystalline ratio of preferably at least 50%, more preferably 70–100%.

The antimicrobial composition used in the present invention is mainly formed from crystalline silicon dioxide as is clearly revealed by the later mentioned X-ray diffraction analysis. Said main component of silicon dioxide comprises preferably at least 70 wt %, more preferably at least 75 wt %, most preferably at least 79 wt % of the crystalline antimicrobial composition of the present invention. Additionally, the crystalline antimicrobial composition may contain preferably 15 wt % or less of aluminum oxide ($Al_2O_3$), more preferably 11 wt % or less and, most preferably 8 wt % or less. Further, zinc and copper can be used as a biocidal metal together with silver.

Silver must be contained as a biocidal metal in the crystalline silicon dioxide composition used in the present antimicrobial polymer composition. Silver ions comprise preferably at least 0.3 wt %, more preferably at least 0.5 wt %, most preferably at least 1 wt % of the crystalline silicon dioxide composition. The crystalline silicon dioxide composition used in the present antimicrobial polymer composition can contain silver ions solely or silver ions and at least one type of biocidal metal ion selected from the group consisting of zinc ions and copper ions as biocidal metal ions.

When zinc ions and copper ions are present, a preferable amount thereof is 1–5 wt % and 0.3–4 wt %, respectively.

The crystalline antimicrobial composition can comprise non-biocidal metal ions having a valence of 1 to 3.

The crystalline antimicrobial composition has a bulk density in the range of from 0.4 to 1.4, preferably from 0.45 to 1.3.

The crystalline antimicrobial composition is porous and has a large specific surface area(SSA). Preferably, it has a pore volume of at least 0.3 $cm^3/g$, and one having a pore volume(PV) of from 0.4 to 1.0 $cm^3/g$ is preferred. Preferably, the crystalline antimicrobial composition has a SSA of at least 5 $cm^2/g$, and one having a SSA of from 25 to 450 $cm^2 l/g$ is more preferred. A SSA is measured by the $N_2$ gas adsorption method of BET method and PV is measured by the mercury porosimeter.

The process for producing the antimicrobial composition used in the present invention is described below.

An antimicrobial composition having an antimicrobial coat of an aluminosilicate on the surface of a silica gel wherein said aluminosilicate containing silver ions and one or two optional metal ions selected from the group consisting of zinc and copper is used as a starting material. Said starting material can contain non-biocidal metal ions having valences of 1 to 3 or ammonium ions.

The process for preparing said starting material is well known and briefly stated below.

The process comprises a first step of chemically treating a porous silica gel with an alkali solution and an aluminate solution and then forming an antimicrobial coat on the thus-treated surface of the silica gel and the second step of treating with a salt solution comprising at least one type of antimicrobial metal ion to allow antimicrobial metal ions [$Ag^+$ and optional $Zn^{2+}$ and/or $Cu^{2+}$] to be retained in the aluminosilicate coat so that an antimicrobial coat is formed. In the first step, aluminic acid ions [$Al(OH)_4^-$;$AlO_2\cdot 2H_2O$] react with $Si(OH)_4$ [$SiO_2\cdot 2H_2O$ as a monomer] present on a surface of pores (micro pore and/or macro pore) in the silica gel to form negatively charged aluminosilicate ions.

A firm ionic bond is formed between alminosilicate ions and porous silica gel so that the release of the former from the later gel body is completely prevented. In the second step, an ion-exchange treatment is carried out in order to retain antimicrobial and/or microbial ion of $Ag^+$ and optional $Zn^{2+}$ and $Cu^{2+}$ ions in the thin aluminosilicate layer. By performing above process, antimicrobial metal ions are exchanged with ion-exchangeable metal ion in the aluminosilicate layer and thus formed antimicrobial layer is fixed strongly on the surface of the silica gel pores. Through the above procedure, the starting material of the crystalline antimicrobial composition used in the present invention is prepared.

A predetermined amount of necessary antimicrobial metal ions in the starting material is able to present in the form of single metal ion or composite metal ions, i.e. $Ag^{+-Zn2+}$, $Ag^+-Cu^{2+}$, and $Ag^+-Zn^{2+}-Cu^{2+}$. In addition to the above metal ions, the starting material is allowable to contain non-biocidal metal ion having valences of 1 to 3, such as monovalent alkali metal ions, nickel and other alkaline earth metal ions with divalent, trivalent rare earth elements [lanthanoid elements: $Ln^{3+}$, elements having an atomic number of from 58 to 71, 21 (Sc), 39(Y) and 57(La)] and zirconium (in a form of zirconyl:$ZrO^{2+}$). Furthermore, said starting material can contain ammonium ions, such as $NH_4^+$, $C_7H_{15}N_2^+$, $C_3H_{16}N^+$, $Me_4N^+$(TMA:tetramethylammonium ion), $Et_4N^+$(TEA:tetraethylammonium ion), and $Pr_4N^+$((TPA:tetrapropylammonium ion).

The presence of non-biocidal ions in the starting material contributes to an improvement of physical properties as well as antimicrobial effects of the finally formed antimicrobial composition, as later mentioned in detail.

As for raw material, an amorphous antimicrobial composition comprising a silica gel body is prepared by the above-mentioned process and comprises a silica as a major component thereof. It comprises preferably at least 70 wt % of $SiO_2$ and 15 wt % or less of alumina ($Al_2O_3$). It further comprises antimicrobial metal ions, such as Ag, Zn and Cu, and non-biocidal metal ions having a valence of 1 to 3. Such an antimicrobial composition has a large SSA, leading to high porous. Furthermore, all of components have good heat resistance. Accordingly, such an antimicrobial composition is preferable as a starting material for the preparation of the present antimicrobial composition. A form of the starting material is not restricted and it can be used as a fine powder, a ground particle or a formed body.

The SSA of the porous starting material is large enough with a SSA value of 350–600 $m^2$/g. Since all of said components are structured of inorganic substances, the starting material has excellent heat resistance. Accordingly, when the starting material is heat treated and crystallized, there is no loss of each inorganic component and the chemical composition remains unchanged. When such a starting material is used, the decrease in SSA and PV is kept to a preferable degree and the thus-obtained particles can be fined easily. Such a process leads to increase in a biocidal rate of the obtained antimicrobial composition.

It is stated that the staring material can contain ammonium ions. This is sometimes preferable due to the following advantageous effects.

The silica gel containing $NH_4^+$ is used as a starting material in the after mentioned working example 11. When a crystallization step is carried out by sintering at high temperature, a decomposition gas is generated and micro voids are produced in the body. The formation of the micro voids make the obtained antimicrobial composition more porous and inhibit a decrease in SSA, so that the produced antimicrobial composition has a preferable bulk density and SSA level. Such an antimicrobial composition is possible to contact with fungi effectively and its biocidal rate is increased. As already noted, the starting material containing non-biocidal metal ions can be used. In the after-mentioned working examples, the amorphous antimicrobial composition containing zirconyl ions ($ZrO^{2+}$), rare earth element ions (lanthanum ion ;$La^{3+}$) and divalent metal ions (calcium ion ;$Ca^{2+}$) are used as starting materials of the samples 9, 10 and 12, respectively. When these materials are sintered and converted to a crystalline antimicrobial composition, the presence of $Zr^{2+}$, $La^{3+}$ or $Ca^{2+}$ ion improves heat resistance, weatherability and resistance to discoloration. Furthermore, biocidal ability is increased because of the difference in bonding energies between antimicrobial metal ions ($Ag^+$, $Zn^{2+}$ and $Cu^{2+}$) and non-biocidal metal ions ($La^{3+}$ and $ZrO^{2+}$).

The crystalline antimicrobial composition can be prepared from said amorphous antimicrobial composition by carrying out the following two step heat treatment.

The first step of the treatment involves keeping the temperature from 250° to 500° C. under atmospheric pressure or vacuum pressure to substantially remove water contained in an antimicrobial composition. The second step is to sinter the composition at high temperature to convert the amorphous antimicrobial composition to a crystalline antimicrobial composition. In this case, a sintering temperature and sintering time vary depending on the composition of the starting material. Generally, the treatment is carried out at a temperature of from 800° to 1300° C. for 1 to 3 hours. By means of the above treatment, an crystalline antimicrobial composition comprising crystalline silicon dioxide as a major component is prepared.

The expression "to substantially remove almost amount of water contained in an antimicrobial composition" means to remove water adsorbed on the surface of the composition.

The temperature during the second treatment step is in the range of from 800° to 1300° C., preferably. When the temperature is below 800° C., crystallization is not fully accomplished. An antimicrobial polymer composition comprising the obtained antimicrobial composition has less weatherability. When the temperature is higher than 1300° C., crystallization is fully accomplished. However, if the sintering is carried out at a temperature higher than 1300° C., the antimicrobial ability of the obtained composition tends to decrease. Accordingly, it is preferable to conduct sinter at the temperature below 1300° C. to inhibit a decrease of antimicrobial ability of the obtained composition. The more preferable temperature range for the second step treatment is from 850° to 1200° C.

The sintered product is coagulated and is glassy or in ceramic from. It is ground or granulated to a predetermined particle size. A bulk density of the ground crystalline antimicrobial composition varies depending on the physical properties and composition of the starting material or temperature of the heat-treatment. Preferably, the bulk density is in the range of from 0.4 to 1.4. Because such a crystalline antimicrobial composition has excellent biocidal ability. Furthermore, such a crystalline antimicrobial composition is preferable for combining with a polymer to provide a uniform mixture having a good dispersibility.

It is preferable that the crystalline antimicrobial composition is used in a form of powder. It is preferable that a content of the crystalline antimicrobial composition is at least 0.2 wt %.

Both halogenated and non-halogenated organic polymers may be used in preparing the antimicrobial polymer composition of the present invention. Non-halogenated organic polymers may be synthetic or semi-synthetic and include the following:

Thermoplastic synthetic polymers such as polyethylene, polypropylene, polystyrene, polyamide, polyesters, polyvinyl alcohol, polycarbonates, polyacetals, ABS resins, acrylic resins, fluorine resins, polyurethane elastomers and polyester elastomers; thermosetting synthetic polymers such as phenolic resins, urea resins, melamine resins, unsaturated polyester resins, epoxy resins and urethane resins; and regenerated or semi-synthetic polymers such as rayon, cuprammonium rayon, cellulose monoacetate, cellulose diacetate and cellulose triacetate. If a strong antimicrobial and/or microbicidal effect is necessary, the polymer composition is preferably foamed or otherwise shaped into a net, a fiber, etc. Preferred from this viewpoint are organic or fiber-forming polymers such as synthetic polymers exemplified by nylon 6, nylon 66, polyvinyl alcohol, polyethylene terephthalate, polybutylene terephthalate, polyacrylonitrile, polyethylene, polypropylene and copolymers thereof, and regenerated or semi-synthetic polymers exemplified by rayon, cuprammonium rayon, cellulose monoacetate, cellulose diacetate and cellulose triacetate. Halogenated organic polymers that can be used in the present invention also are not limited to any particular kinds and may be exemplified by polyvinyl chloride and polyvinylidene chloride.

The time at which the silica gel based antimicrobial composition is added to the polymer and the method by which it is added are not limited in any particular way in the present invention. For example, the antimicrobial composition may be mixed with a starting monomer and the mixture is then polymerized. In another method, the composition may be mixed with a reaction intermediate and the mixture is then polymerized. Alternatively, the composition may be mixed with the complete polymer, if desired, the silica gel based antimicrobial composition is mixed with polymer pellets or a master batch is prepared from a polymer containing said composition and the mixture or master batch is shaped to a desire form. In still another method, the antimicrobial composition is mixed with a molding dope, for example, a spinning solution. The procedure of these method is hereinafter referred to simple as "mixing the silica gel based antimicrobial composition with a polymer or adding it to the polymer".

A suitable method may be adopted taking into account the characteristics of the polymer used and process conditions. In ordinary cases, the silica gel based composition is desirably mixed with the polymer just before molding. However, in order to insure more efficient dispersion of the silica gel based antimicrobial composition, it may be mixed with a monomer. Prior to addition to a polymer, the antimicrobial composition may advantageously be dried or heat-treated as already mentioned hereinabove. When a predetermined amount of the antimicrobial composition is to be added to a polymer, the atmosphere (e.g. an oxidizing atmosphere such as the air or an inert gas atmosphere such as $N_2$ or $CO_2$), the temperature for mixing or the mixing time may be held at preferred conditions in accordance with the specific characteristics of the polymer used. The silica gel based antimicrobial composition is preferably used in an amount of 0.01–20 wt % of the total weight of the polymer composition. If the content of the silica gel based composition is less than 0.01 wt % of the total weight of the polymer composition, the antimicrobial and/or microbicidal activity of the polymer composition is often unsatisfactory against common bacteria and fungi. If the content of the silica gel based composition is more that 20 wt % of the total weight of the polymer composition, the antimicrobial and/or microbicidal activity of the resulting polymer composition is saturated and any further addition of the silica gel based composition will not contribute to an improved antimicrobial and/or microbicidal action. Furthermore, excessive addition of the silica gel based composition has the potential to deteriorate the physical properties of the finally obtained polymer composition.

The particle size of the silica gel based antimicrobial composition that is advantageously used to produce the antimicrobial polymer composition of the present investigation is discussed below.

While there is no particular limitation on the particle size of said composition, there is of course a preferred range depending on the specific use of the final product. For example particles of the antimicrobial composition with sizes of 548–149 micro meter (30–100 mesh) can be used for mixing with the polymer but in order to insure more uniform dispersion in the polymer, smaller particles, for example, those having sizes of 74 micro meter (200 mesh) or much finer particles with sizes of from several micro meters to less than a hundred micrometers, may be used.

The particle size of the antimicrobial composition may be adjusted by selecting the particle size of the starting silica gel and by pulverizing the prepared silica gel based antimicrobial composition with a mill that is selected as appropriate for a specific purpose. When the antimicrobial polymer composition of the present invention is a shaped part having a certain thickness, for example, in the case where it is to be applied to various types of containers, pipes, granules of filaments of large denier, the silica gel based antimicrobial composition may have particle sizes of up to less than a hundred to less than a thousand micro meters or even more. If, on the other hand, the polymer composition is to be shaped into fibers of fine denier or thin films, the particle size of the silica gel based antimicrobial composition is desirably small. For example, in the case of manufacturing fibers for apparel, particle sizes of not more than 6 micro meter are preferred.

In addition to the silica gel based antimicrobial composition, the antimicrobial polymer composition of the present invention may contain other ingredients that are commonly used in the art. Examples of such secondary ingredients include: polymerization catalysts, stabilizers, weathering (lightfast) agents, compounding agents, antioxidants, activators, matting agents, foaming agents, flame retardants, modifiers, brighteners, pigment (colorants), inorganic or organic fillers, various plasticizers, and lubricants. These additives may be incorporated as required. The antimicrobial polymer composition of the present invention may also contain liquids or organic solvents. When said composition is to be used as a shaped part, its shape and size are in no way limited. In order to provide the shaped part with an antimicrobial and/or microbicidal activity, it may be imparted to the whole part of the polymer, or if desired, to only part thereof. When the microbicidal polymer composition of the present invention is shaped part, its microbicidal action is considered to be largely dependent on the silica gel based antimicrobial composition present near the surface of the shaped part, so it may be advisable to provide the shaped part with a multilayer structure and treat its outer layer to acquire a microbicidal activity. In the case of fibers, a core/sheath yarn may be prepared by a known conjugate fiber spinning technique, with the antimicrobial polymer composition of the present invention being used as the sheath component.

The antimicrobial polymer composition of the present invention keeps excellent biocidal ability for a long time and shows good weatherability. It shows little coloration or discoloration over time. Furthermore, since the antimicrobial polymer composition of the present invention has a good water-resistance, it shows little change in water or hot water over time.

The antimicrobial polymer composition of the present invention has the following advantages:

(1) Although a structure of the starting material of silica-based amorphous antimicrobial composition is destroyed by high temperature sintering, SSA and bulk density are kept within the desired range. Accordingly, the obtained particles exhibit an excellent antimicrobial effect against fungi. They also exhibit good mildewcidal effects. Although a biocidal rate of the antimicrobial composition of the present invention is somewhat slower than that of the starting material, i.e. a silica-based amorphous antimicrobial composition, it shows excellent antimicrobial effects. The important advantageous effects of the crystalline antimicrobial composition used in the present invention are that it has excellent heat resistance, weatherability, light-resistance and discoloration resistance. The crystalline antimicrobial composition of the present invention is stable at the temperature of 1200°–1300° C. Discoloration of the composition is not observed. A structure of the present crystalline antimicrobial composition is stable against light and a light-resistance is extremely large. Accordingly, when the crystalline antimicrobial composition is mixed with a polymer, a composition having excellent antimicrobial effects, weatherability, light-resistance and discoloration resistance is obtained.

The present invention is described in detail by working examples, however they are not intended to restrict the scope of the present invention.

EXAMPLE 1

This example shows a process for preparing the crystalline antimicrobial composition used in the present invention.

The starting materials of antimicrobial composition in the working examples 1–7 are silica gel based antimicrobial composition. It comprises 70 wt % or more of $SiO_2$ and 15 wt % or less of $Al_2O_3$. It comprises Ag and Zn as antimicrobial metals. It further comprises a small amount of monovalent alkali metal ($Na^+$) as a non-antimicrobial metal ion. The above powdery starting material is preheated at 350° C. for 1 hour as shown in Table 1, to substantially remove water. A high temperature sintering step is carried out at 800°–1200° C. for 1 or 2 hours as shown in Table 1 and a crystalline antimicrobial composition is obtained. The obtained clump of sintered body is ground and then finely milled with a JET mill. The samples 1–7 which comprise the crystalline antimicrobial composition of the invention comprise 83.38 wt % of $SiO_2$ and 7.56 wt % of $Al_2O_3$, and 3.6–3.7 wt % of Ag and 2.0 wt % of Zn. An average particle size (Dav) of the fine antimicrobial composition particles is in the range of 2.9–8.3 micrometers, and their bulk densities are in the range of 0.40–1.00($d_1$) and 0.46–1.10($d_2$), as represented in Table 1, wherein $d_1$ and $d_2$ represent a lightly packed bulk density and bulk density packed under vibration, respectively. The method for determining them is as follows:

To attain a lightly packed bulk density, a powder is placed in a 200 milliliter graduated cylinder, lightly vibrated, and the volume and weight of the powder are measured after it has settled.

To attain a bulk density packed under vibration, a powder is put into a 200 milliliter graduated cylinder under vibration, and further vibrated after the powder has settled, with the final volume and weight of the powder, then being measured.

Sample 8 was prepared by the same procedure as that for preparing sample 7 except that the starting material is an antimicrobial composition having a silica gel body ($SiO_2$= 82.01 wt % and $Al_2O_3$=7.56%) and 7.2 wt % of Ag as antimicrobial metal and trace amount of $Na^+$ as monovalent metal. The Dav of the pulverized final product is 5.1 micro meters and the $d_1$ and $d_2$ are 0.94 and 1.05, respectively.

Under the condition shown in the table, sample 9 was prepared by carrying out heat treatment to recrystallize the staring material of an antimicrobial composition having a silica gel body ($SiO_2$=83.95 wt % and $Al_2O_3$=7.56%) and containing 3.0 wt % of Ag as an antimicrobial metal, 1.9 wt % of Zr in the form of $ZrO^{2+}$ (zirconil ion) as a non-biocidal ion and a trace amount of $Na^+$. The Dav of the pulverized final product of sample 9 is 4.2 micro meters and the $d_1$ and $d_2$ are 0.71 and 0.86, respectively.

Under the condition shown in the table, sample 10 was prepared by carrying out heat treatment to recrystallize the staring material of an antimicrobial composition ($SiO_2$= 80.89 wt % and $Al_2O_3$=7.56 wt %) having a silica gel body and containing 3.0 wt % of Ag as an antimicrobial metal, 4.8 wt % of $La^{3+}$, which is a typical lanthanoid element, as a non-biocidal ion and a trace amount of $Na^+$. The Dav of the pulverized final product of sample 10 is 6.8 micro meters and the $d_1$ and $d_2$ values are 0.98 and 1.21, respectively.

Sample 11 was prepared by carrying out the two step heat treatment of the first at 350° C. for 1 hour and the second at 1100° C. for 2 fours employing a starting material of an antimicrobial composition ($SiO_2$=79.68 wt % and $Al_2O_3$= 7.56 wt %) having a silica gel body and comprising 4.0 wt % of Ag and 2.9 wt % of Zn as antimicrobial metals, 3.5 wt % of $NH_4^+$, which is a typical ammonium ion, as a non-biocidal ion and a trace amount of $Na^+$. The Dav of the pulverized final product of sample 11 is 4.5 micro meters and the $d_1$ and $d_2$ values are 1.01 and 1.19, respectively.

Under the condition shown in the table, sample 12 was prepared by carrying out heat treatment to recrystallize the starting material of an antimicrobial composition ($SiO_2$= 81.85 wt % and $Al_2O_3$=7.56 wt %) having a silica gel body and containing 2.98 wt % of Ag, 2.01 wt % of Zn and 0.47 wt % of Cu as antimicrobial metals, 2.11 wt % of $Ca^{2+}$ as a divalent non-biocidal ion and a trace amount of $Na^+$. The Dav of the pulverized final product of sample 12 is 8.0 micro meters and the $d_1$ and $d_2$ values are 1.06 and 1.25, respectively.

The comparative sample 1 is an amorphous antimicrobial composition having a silica gel body and comprising 3.6 wt % of Ag and 2.0 wt % of Zn. This is used for the starting material of the samples 1–6, while the comparative sample 2 is an amorphous antimicrobial composition having a silica gel body and comprising 3.6 wt % of Ag and 2.2 wt % of Zn. The bulk densities of the present antimicrobial composition are very large compared with those of comparative examples 1 and 2.

FIG. 1 shows an X-ray diffraction spectrum of the antimicrobial composition of sample 7 (Ag=3.7% and Zn=2.0%; Dav=3.77 micro meters). The analysis reveals that a major crystalline structure of the composition is $SiO_2$.

It is recognized from the X-ray diffraction spectrum that crystalline of $Zn_2SiO_4$, $ZnSiO_3$, $Al_{16}Si_2O_{1.3}$, $Al_2SiO_5$, $Al_2Si_{44}O_{10}$, $Ag_2SiO_3$, $Zn_2SiO_4$, $Ag_4SiO_4$ and $Ag_4Al_{22}O_{37}$ are also contained in the antimicrobial composition. Furthermore, the existence of Ag and Zn as biocidal metals is also confirmed.

200-ml volumetric flask. When *Escherichia coli* was tested, 15 mg of the sample was used and when *Aspergillus niger* was tested, 50 mg of the sample was used. The test fungi or bacteria suspension was added to make a total volume of 100 ml and a number of cells were adjusted to those represented in Tables 2 and 3. The flask was shaken at 25° C.+/−1° C. and a number of viable cells were measured at predetermined periods.

It can be seem from the result shown in Table 2, that the antimicrobial compositions of samples 1–5, 8 and 10 (Dav= 2.9–6.8 micro meters) killed almost all *E. coli* in a short period, i.e. within about 60 minutes. The control examples 1 and 2 were blank tests, carried out without an antimicrobial composition.

Table 3 represents a result of a measurement of antimicrobial power against *A. niger*. In this case, the antimicrobial

TABLE 1

| Sample No. | Heat treatment First step | Heat treatment Second step | Content of primary metals contained in the obtained antimicrobial composition % (anhydrous basis) | Bulk density of antimicrobial composition $d_1$ | Bulk density of antimicrobial composition $d_2$ | Average particle size of pulverized antimicrobial composition Dav, μm |
|---|---|---|---|---|---|---|
| 1 | 350° C. - 1 hr | 800° C. - 1 hr | Ag = 3.6; Zn = 2.0 | 0.41 | 0.53 | 2.9 |
| 2 | 350° C. - 1 hr | 800° C. - 2 hr | Ag = 3.6; Zn = 2.0 | 0.40 | 0.46 | 3.1 |
| 3 | 350° C. - 1 hr | 900° C. - 1 hr | Ag = 3.6; Zn = 2.0 | 0.56 | 0.65 | 3.7 |
| 4 | 350° C. - 1 hr | 900° C. - 2 hr | Ag = 3.6; Zn = 2.0 | 0.68 | 0.83 | 3.9 |
| 5 | 350° C. - 1 hr | 1000° C. - 1 hr | Ag = 3.6; Zn = 2.0 | 0.83 | 1.10 | 5.3 |
| 6 | 350° C. - 1 hr | 1200° C. - 2 hr | Ag = 3.6; Zn = 2.0 | 0.82 | 1.14 | 8.3 |
| 7 | 350° C. - 1 hr | 1000° C. - 2 hr | Ag = 3.7; Zn = 2.0 | 1.00 | 1.10 | 3.77 |
| 8 | 350° C. - 1 hr | 1000° C. - 2 hr | Ag = 7.2 | 0.94 | 1.05 | 5.1 |
| 9 | 350° C. - 1 hr | 900° C. - 2 hr | Ag = 3.0; Zn = 1.9 | 0.71 | 0.86 | 4.2 |
| 10 | 350° C. - 1 hr | 1100° C. - 1 hr | Ag = 3.0; La = 4.8 | 0.98 | 1.21 | 6.8 |
| 11 | 350° C. - 1 hr | 1100° C. - 2 hr | Ag = 4.0; Zn = 2.9 | 1.01 | 1.19 | 4.5 |
| 12 | 350° C. - 1 hr | 1100° C. - 1 hr | Ag = 2.98; Zn = 2.01; Cu = 0.47; Ca = 2.11 | 1.06 | 1.25 | 8.0 |
| C - 1 | dried sample | — | Ag = 3.6 ; Zn = 2.0 | 0.30 | 0.33 | 2.7 |
| C - 2 | dried sample | — | Ag = 3.6 ; Zn = 2.2 | 0.31 | 0.33 | 2.6 |

C: Comparative Examples
$d_1$: lightly packed bulk density
$d_2$: bulk density packed under vibration

EXAMPLE 2

The antimicrobial power of the crystalline antimicrobial composition of the present invention is discussed below.

To prepare a cell suspension of bacterium, the cells of a test bacterium (*Escherichia coli*) that had been cultivated in an agar medium at 37° C. for 18 hours were suspended in a phosphate buffer (1/15M, pH=7.2) at a concentration of $10^6$ cells/ml and diluted appropriately for the test.

To prepare a cell suspension of fungus, the conidia of the test fungus that had been cultivated in a potato dextrose agar medium at 25° C. for 7 days were suspended in sterile 0.005% dioctyl sodium sulfosuccinate aqueous solution to prepare a suspension at a concentration of $10^8$ cells/ml and diluted appropriately for the test.

Test bacteria:
*Escherichia coli* IFO-12734
*Aspergillus niger* IFO-4407
Medium
fungi: Sabouraud Dextrose Agar (BBL)
bacteria : Mueller Hinton 2 (BBL)
Test procedure for measuring antimicrobial power:
An antimicrobial sample in the form of a fine powder was determined by "shake flask method (S.F. method)." A predetermined amount of dried fine powder of antimicrobial composition was added to a phosphate buffer solution in a power was measured by a shake flask method with $10^5$ cells/ml of an initial count of *A. niger* cells and 50 mg/100 ml of a concentration of the antimicrobial composition. As shown in the table, a preferable result was obtained. The sample 2 was sintered at 800° C. for 2 hours and sample 3 was sintered at 900° C. for 1 hour. Both samples 2 and 3 exhibit good antimicrobial activity and almost all *A. niger* was killed within 8 hours. The sample 3, which was sintered at a temperature above 1000° C., has less antimicrobial power against *A. niger* than that of the samples 2 or 3. The comparative example 1 shown in the table 3 is the same sample as in table 1.

It is obvious from the results shown in the tables 2 and 3, that the crystalline antimicrobial composition comprising crystalline silicon dioxide as a principal component shows satisfactory antimicrobial power against common fungus and bacterium.

Samples 4, 6 and 10, which are within the scope of the crystalline antimicrobial composition used in the present invention, were press molded. Furthermore, a known antimicrobial zeolite having A-Zeolite body containing $SiO_2$ and $Al_2O_3$ at a molar ratio of $SiO_2/Al_2O_3$=1.99 and comprising 3.4 wt % of Ag and 6.9 wt % of Zn was also press molded. The press molded test pieces have a diameter of 30 mm and a thickness of 5 mm. The samples were exposed to UV radiation (365 nm) for 500 hours under the same conditions. No discoloration was observed and no change occurred with time with respect to the 3 samples. On the other hand, with respect to the comparative sample of the known antimicrobial zeolite discoloration was observed after 140–150 hours. It is revealed from the above UV test that a crystalline antimicrobial composition of the present invention has excellent weatherability.

were prepared as samples 13–20. The samples 13–15 employ sample 7 (Dav=3.77 micro meter). The sample 16 employ sample 12 (Dav=8.0 micro meter). The samples 17, 19 and 20 comprise sample 6 and titanium dioxide ($TiO_2$) or zirconium oxide($ZrO_2$) and TBZ(thiabendazole : $C_{10}H_7N_3S$). The additives prevent the antimicrobial poly-

TABLE 2

Measuring method: shake flask method (S.F. method)
Bateria: *Escherichia coli* (IFO 12734)
Initial cell count: $10^5$/ml
Total liquid volume: 100 ml

| | | Antimicrobial composition | | Number of viable cells per ml | | | |
|---|---|---|---|---|---|---|---|
| | | Amount | Antimicrobial metal | | | | |
| Sample No. | Dav, μm | mg/100 ml | content mg/100 ml | 0 min. | 20 min. | 60 min. | 180 min. |
| 1 | 2.9 | 15 | Ag = 0.54; Zn = 0.30 | $2.1 \times 10^5$ | 0 | 0 | — |
| control - 1 | — | — | — | $2.1 \times 10^5$ | $1.8 \times 10^5$ | $1.7 \times 10^5$ | — |
| 2 | 3.1 | 15 | Ag = 0.54; Zn = 0.30 | $3.2 \times 10^5$ | 0 | 0 | 0 |
| 3 | 3.7 | 15 | Ag = 0.54; Zn = 0.30 | $3.2 \times 10^5$ | 0 | 0 | 0 |
| 4 | 3.9 | 15 | Ag = 0.54; Zn = 0.30 | $3.2 \times 10^5$ | — | — | 2 |
| 5 | 5.3 | 15 | Ag = 0.54; Zn = 0.30 | $3.2 \times 10^5$ | $9.1 \times 10^4$ | 5 | 3 |
| 8 | 5.1 | 15 | Ag = 1.1 | $3.2 \times 10^5$ | 0 | 0 | 0 |
| 10 | 6.8 | 15 | Ag = 0.45 | $3.2 \times 10^5$ | $1.1 \times 10^1$ | 6 | 0 |
| control - 2 | — | — | — | $3.2 \times 10^5$ | $3.4 \times 10^5$ | $2.4 \times 10^5$ | $2.2 \times 10^5$ |

TABLE 3

Measuring method: shake flask method (S.F. method)
Fungi: *A. niger* (IFO 4407)
Initial cell count: $10^5$/ml

| | | Antimicrobial composition | | Number of viable cells per ml | | |
|---|---|---|---|---|---|---|
| | | Amount | Antimicrobial metal | | | |
| Sample No. | Dav, μm | mg/100 ml | content mg/100 ml | 0 hr | 3 hr | 8 hr |
| 2 | 3.1 | 50 | Ag = 1.8; Zn = 1.0 | $1.4 \times 10^5$ | $1.3 \times 10^2$ | 0 |
| 3 | 3.7 | 50 | Ag = 1.8; Zn = 1.0 | $1.4 \times 10^5$ | $1.8 \times 10^3$ | 9 |
| 5 | 5.3 | 50 | Ag = 1.8; Zn = 1.0 | $1.4 \times 10^5$ | $7.7 \times 10^4$ | $2.3 \times 10^4$ |
| C - 1 | 2.7 | 50 | Ag = 1.8; Zn = 1.0 | $1.4 \times 10^5$ | 5 | 0 |
| control | — | — | — | $1.4 \times 10^5$ | — | $2.7 \times 10^5$ |

C - 1: Comparative Examples 1

EXAMPLE 3

This example shows a process for preparing a present invention's antimicrobial polymer composition comprising crystalline antimicrobial composition.

K-1008N available from Chisso Corp. is used as polypropylene(PP) and L1225W available from Teijin Kasei Corp. is used as polycarbonate(PC).

Polymers were preheated to remove water adsorbed on a surface of the polymers. After that, a predetermined amount of crystalline antimicrobial composition was added. The obtained mixture was heated to a predetermined temperature, kneading and molded. The predetermined temperature was from 180° to 190° C. for PP and from 280° to 290° C. for PC. The moldings were cut into two kinds of test pieces, one is 50 mm×50 mm, from 1.5 to 2 mm thick and another is 25 mm×25 mm, from 1.5 to 2 mm thick. The former was used in a discoloration test and the later was used in an antimicrobial ability test.

The antimicrobial PP compositions employing the crystalline antimicrobial compositions prepared in Example 1 mer composition from a discoloration with time and improve weatherability thereof. The samples 18 employs sample 10 (Dav=6.8 micro meter).

The antimicrobial PC compositions employing the crystalline antimicrobial compositions prepared in Example 1 were prepared as samples 21–24. The sample 21 employs sample 1 (Dav=2.9 micro meter). The samples 22–24 comprise the crystalline antimicrobial composition and titanium dioxide($TiO_2$) or TBZ. The additives improve a weatherability of antimicrobial polymer composition. TBZ extremely increases a water resistance of the composition under a wet condition and prevents them from discoloring.

EXAMPLE 4

The antimicrobial power of the antimicrobial polymer composition of the present invention is discussed below.

A sample piece having a size of 25 mm×25 mm was used in the test.

An antimicrobial ability of the antimicrobial polymer compositions was measured by the following "Drop method".

1) The tested bacterium or fungus
   *Escherichia coli* (IFO 12734)
   *Staphylococcus aureus* (IFO 12732)
2) Preparation of the suspension of the tested bacterium or fungus
   The cells of bacterium or fungus that had been cultivated in Nutrient Agar (Oxoid) at 35° C. for 18–24 hours were suspended in sterile phosphate buffer at a concentration of $10^5$ cells/ml.
3) Medium
   Mueller Hinton Medium (Difco): 35° C. for 2 days
4) Preparation of the test piece
   25 mm×25 mm sized test piece was cleaned with alcohol-impregnated cotton and air-dried. The obtained test piece was provided to the test.
5) Test procedure
   0.3 ml of the suspension of the tested bacterium or fungus was dropped on a surface of the test piece. The test piece was stood for a given time. At 8 and 24 hours later, a number of viable cells was counted by mixed plate culture method.

The result of the test was shown in the table 4. The antimicrobial polymer compositions of the samples 13–16 and 18 exhibit an excellent antimicrobial power against *E. coli*. Twenty-four hours later, a number of viable cells per plate of the test piece was less than 10 cells in all cases. The death rate was greater than 99.99%. Sample 17, which further comprises titanium dioxide and TBZ, also exhibits an excellent antimicrobial power against *E. coli*. Twenty-four hours later, a number of viable cells per plate of the test piece was less than 10 cells.

Antimicrobial powers of the samples 19 and 20 against *S. aureus* were measured with "Drop method". The sample 19 comprises 4 wt % of sample 6, 0.5 wt % of $TiO_2$ and 0.2 wt % of TBZ. The sample 20 comprises 3.0 wt % of sample 6, 2.1 wt % of $ZrO_2$ and 0.2 wt % of TBZ. A number of viable cells at 24 hours later was less than 10 cells for sample 19 and $3.9 \times 10^2$ cells for sample 20. The death rates were greater than 96% in both cases.

An antimicrobial power each of samples 21–24 was measured against *E. coli* and *S. aureus*. The samples 21–24 were antimicrobial PC compositions. The sample 21 comprises 2.5 wt % of sample 1 and the sample 22 comprises 3 wt % of sample 2 and 0.5 wt % of $TiO_2$. Both samples exhibit an excellent antimicrobial ability against *E. coli*. 24 hours later, a number of viable cells was less than 10 cells for sample 21 and less than 30 cells for sample 22.

The sample 23 comprises 2.5 wt % of sample 1 and 0.2 wt % of TBZ and the sample 24 comprises 3 wt % of sample 6 and 0.5 wt % of $TiO_2$. Both samples exhibit an excellent antimicrobial ability against *E. coli* and *S. aureus*. Twenty-four hours later, the death rates were greater than 96% against *E. coli* and *S. aureus* in both cases.

This example reveals that the antimicrobial polymer composition of the present invention has an excellent antimicrobial ability.

TABLE 4

Test method: Drop method
Bacteria or fungi: *E. coli* (IFO 12734); *S. aureus* (IFO 12732)
PP: Chisso K-1008N
PC: L1225W
Initial cell count: $10^5$ cells/ml

| Sample No. | Kind of polymer | Sample No. of antimicrobial composition | Composition of antimicrobial polymer | Bacteria or fungi | *Number of viable cells (hr) 0 | 8 | 24 |
|---|---|---|---|---|---|---|---|
| 13 | PP | 7 | PP-B-7, 5% | *E. coli* | $1.8 \times 10^5$ | <10 | <10 |
| 14 | PP | 7 | PP-B-7, 4% | *E. coli* | $1.8 \times 10^5$ | <10 | <10 |
| 15 | PP | 7 | PP-B-7, 3% | *E. coli* | $1.8 \times 10^5$ | $8.5 \times 10^2$ | <10 |
| 16 | PP | 12 | PP-B-12, 3% | *E. coli* | $1.8 \times 10^5$ | — | <10 |
| — | PP-BL(1) | — | PP without antimicrobial composition | *E. coli* | $1.8 \times 10^5$ | — | $3.8 \times 10^5$ |
| 17 | PP | 6 | PP-B-6, 3%-$TiO_2$, 0.5%-TBZ, 0.2% | *E. coli* | $1.0 \times 10^5$ | — | <10 |
| 18 | PP | 10 | PP-B-10, 3% | *E. coli* | $1.0 \times 10^5$ | — | <10 |
| — | PP-BL(2) | — | PP without antimicrobial composition | *E. coli* | $1.0 \times 10^5$ | — | $9.2 \times 10^4$ |
| 19 | PP | 6 | PP-B-6, 4%-$TiO_2$, 0.5%-TBZ, 0.2% | *S. aureus* | $1.1 \times 10^5$ | — | <10 |
| 20 | PP | 6 | PP-B-6, 3.0%-$ZrO_2$, 1%-TBZ, 0.2% | *S. aureus* | $1.1 \times 10^5$ | — | $3.9 \times 10^3$ |
| — | PP-BL(3) | — | PP without antimicrobial composition | *S. aureus* | $1.1 \times 10^5$ | — | $1.6 \times 10^5$ |
| 21 | PC | 1 | PC-B-1, 2.5% | *E. coli* | $1.6 \times 10^5$ | — | <10 |
| — | PC-BL(1) | — | PP without antimicrobial composition | *E. coli* | $1.6 \times 10^5$ | — | $7.7 \times 10^5$ |
| 22 | PC | 2 | PC-B-2, 3%-$TiO_2$, 0.5% | *E. coli* | $2.9 \times 10^5$ | — | 30 |
| 23 | PC | 6 | PC-B-6, 2.5%-TBZ, 0.2% | *E. coli* | $2.9 \times 10^5$ | — | $1.3 \times 10^4$ |
| 24 | PC | 6 | PC-B-6, 3%-$TiO_2$, 0.5% | *S. aureus* | $3.0 \times 10^5$ | — | $1.2 \times 10^4$ |
| — | PC-BL(2) | — | PP without antimicrobial composition | *S. aureus* | $3.0 \times 10^5$ | — | $2.0 \times 10^5$ |

*Number of viable cells are counted per sheet of sample
B-1 (sample 1): B-7 (sample 7)
B-2 (sample 2): B-10 (sample 10)
B-6 (sample 6): B-12 (sample 12)

EXAMPLE 5

A stability with time of the antimicrobial polymer composition of the present invention was measured in this example. The test pieces of the samples 15, 17, 20, 25 and 26 were left to stand in a sunny room for 8 months. Sample 15 comprises 3 wt % of sample 7, sample 17 comprises 3 wt % of sample 6, 0.5 wt % of $TiO_2$ and 0.2 wt % of TBZ, sample 20 comprises 3 wt % of sample 6, 1 wt % of $ZrO_2$ and 0.2 wt % of TBZ, sample 25 comprises 2 wt % of sample 6 and 0.5 wt % of talc, and sample 26 comprises 2 wt % of sample 7. The result is shown in Table 5. No coloring nor color difference was observed with respect to all samples. Comparative sample 3 comprise PP and 3 wt % of silica-gel based amorphous antimicrobial composition was prepared.

The silica-gel based amorphous antimicrobial composition contains 3.6 wt % of Ag, 2.0 wt % of Zn and has 2.7 micro meter of average diameter (Dav=2.7 micro meter) and was used as a starting material of the sample 1. The comparative sample 3 was tested under the same conditions as the other samples. Two months later, no coloring was observed. However, after 3 months, a coloring became stronger with time.

The result of the example reveals that the antimicrobial polymer composition of the present invention has good stability.

TABLE 5

| Sample No. | Composition of molded antimicrobial polymer | Initial color | Time after molding (month) 1 2 3 4 5 6 7 8 |
|---|---|---|---|
| 15 | PP—B-7, 3% | white | no coloring is observed (white) → |
| 17 | PP—B-6, 3%-TiO₂, 0.5%—TBZ, 0.2% | creamy white | no color difference is observed (creamy white) → |
| 20 | PP—B-6, 3% —ZrO₂, 1%—TBZ, 0.2% | creamy white | no color difference is observed (creamy white) → |
| 25 | PP—B-6, 2%-, 0.5%—TBZ, 0.2% | creamy white | no color difference is observed (creamy white) → |
| 26 | PP—B-7, 2% | white | no coloring is observed (white) → |
| C-3 | a starting material of PP-sample 1 | | no coloring is observed, after 3 months, coloring became stronger with time (white → discoloration → brown) → | antimicrobial compositions: B-6 (sample 6), B-7 (sample 7)
C-3: comparative example 3

EXAMPLE 6

A wet heat test was carried out with respect to an antimicrobial PC compositions in this example.

The sample 27 comprising 0.3 wt % of sample 7 and 0.1 wt % of TBZ was molded at 280°–290° C. The moldings were cut into small test piece having 50 mm×50 mm and 1.5–2 mm thick. Another test piece was prepared from the sample 28 comprising 1.0 wt % of sample 7 and 0.1 wt % of TBZ under the same procedure. The sample pieces were treated with a superheated stream at 100° C. for 24 hours or 120° C. for 11 hours. After that, L, a, b and delta E values of CIE color system were measured. Those values represent a degree of color difference of the samples. The result was shown in the table 6. The delta E values of the samples 27 and 28 were small. The result shows that the antimicrobial polymer composition of the present invention exhibits a little color change when it is treated with superheated stream.

The result of this example reveals that the antimicrobial polymer composition of the present invention has an excellent water resistance and heat resistance.

TABLE 6

| | | Color difference | | | |
|---|---|---|---|---|---|
| Sample No. | Condition of a wet heat test | L | a | b | Δ E |
| 27 | before treatment | 78.5 | −2.7 | 19.6 | — |
| | 100° C. - 24 hr | 76.8 | −1.6 | 20.0 | 2.0 |
| | 120° C. - 11 hr | 76.5 | −1.8 | 19.4 | 2.2 |

TABLE 6-continued

| | | Color difference | | | |
|---|---|---|---|---|---|
| Sample No. | Condition of a wet heat test | L | a | b | Δ E |
| 28 | before treatment | 66.2 | −1.4 | 25.5 | — |
| | 100° C. - 24 hr | 65.2 | 0.2 | 26.0 | 1.9 |
| | 120° C. - 11 hr | 63.5 | 0.7 | 25.5 | 3.4 |

We claim:

1. An antimicrobial polymer composition comprising a crystalline antimicrobial composition and a polymer, wherein said crystalline antimicrobial composition comprises a crystalline silicon dioxide containing silver ions and optionally one or two metal ions selected from the group consisting of zinc and copper.

2. An antimicrobial polymer composition of claim 1 wherein a content of crystalline silicon dioxide is at least 70 wt % of the crystalline antimicrobial composition.

3. An antimicrobial polymer composition of claim 1 wherein a bulk specific gravity of the crystalline antimicrobial composition is from 0.4 to 1.4.

4. An antimicrobial polymer composition of claim 1 wherein a content of silver ions in the crystalline antimicrobial composition is at least 0.3 wt %.

5. An antimicrobial polymer composition of claim 1 further comprising an additive selected from the group consisting of titanium dioxide, TBZ, zirconia, talc, and mixtures thereof.

6. An antimicrobial polymer composition of claim 1 wherein a content of the crystalline antimicrobial composition is at least 0.2 wt %.

7. A process for preparing an antimicrobial composition of claim 1 comprising steps of 1) preheating an antimicrobial composition having an antimicrobial coating of an aluminosilicate provided on the surface of silica gel, wherein said aluminosilicate contains silver ions and optionally one or two metal ions selected from the group consisting of zinc and copper, to a temperature between 250° and 500° C. to substantially remove water, 2) sintering at a temperature from 800° to 1300° C., and 3) mixing the obtained crystalline antimicrobial composition with a polymer.

* * * * *